United States Patent
Clevenger

(10) Patent No.: US 10,390,533 B2
(45) Date of Patent: Aug. 27, 2019

(54) SURFACES WITH OLIGOMERIC OR POLYMERIC ANTIMICROBIALS

(71) Applicant: Orthobond Corporation, North Brunswick, NJ (US)

(72) Inventor: Randell Clevenger, North Plainfield, NJ (US)

(73) Assignee: ORTHOBOND CORPORATION, North Brunswick, NJ (US)

( * ) Notice: Subject to any disclaimer, the term of this patent is extended or adjusted under 35 U.S.C. 154(b) by 0 days.

(21) Appl. No.: 15/785,765

(22) Filed: Oct. 17, 2017

(65) Prior Publication Data

US 2018/0103642 A1 Apr. 19, 2018

Related U.S. Application Data

(60) Provisional application No. 62/408,912, filed on Oct. 17, 2016.

(51) Int. Cl.
| | | |
|---|---|---|
| *A01N 57/16* | (2006.01) | |
| *C08F 220/36* | (2006.01) | |
| *C09D 133/14* | (2006.01) | |
| *C25D 11/26* | (2006.01) | |
| *C09D 5/14* | (2006.01) | |
| *A01N 43/40* | (2006.01) | |
| *C25D 11/30* | (2006.01) | |
| *C25D 11/34* | (2006.01) | |

(52) U.S. Cl.
CPC ............. *A01N 57/16* (2013.01); *A01N 43/40* (2013.01); *C08F 220/36* (2013.01); *C09D 5/14* (2013.01); *C09D 133/14* (2013.01); *C25D 11/26* (2013.01); *C08F 2438/01* (2013.01); *C25D 11/30* (2013.01); *C25D 11/34* (2013.01)

(58) Field of Classification Search
None
See application file for complete search history.

(56) References Cited

U.S. PATENT DOCUMENTS

| | | |
|---|---|---|
| 4,879,135 A | 11/1989 | Greco et al. |
| 5,078,782 A | 1/1992 | Nielsen et al. |
| 5,126,210 A | 6/1992 | Wieserman et al. |
| 6,284,813 B1 | 9/2001 | Leppard et al. |
| 6,355,704 B1 | 3/2002 | Nakatsuka et al. |
| 6,645,644 B1 | 11/2003 | Schwartz et al. |
| 2002/0040092 A1 | 4/2002 | Siddiqui et al. |
| 2003/0091641 A1* | 5/2003 | Tiller ............... A01N 43/40 424/486 |
| 2004/0023048 A1 | 2/2004 | Schwartz et al. |
| 2004/0171779 A1* | 9/2004 | Matyjaszewski ......... C08F 2/38 526/303.1 |
| 2005/0027360 A1 | 2/2005 | Webb |
| 2005/0147750 A1 | 7/2005 | Jacobs et al. |
| 2006/0194008 A1 | 8/2006 | Schwartz et al. |
| 2007/0077348 A1 | 4/2007 | Lu et al. |
| 2007/0196663 A1 | 8/2007 | Schwartz et al. |
| 2007/0292355 A1 | 12/2007 | Tamarkin et al. |
| 2007/0292477 A1 | 12/2007 | Kumar |
| 2008/0118734 A1 | 5/2008 | Goodwin et al. |
| 2009/0232867 A1 | 9/2009 | Domb et al. |
| 2010/0215643 A1* | 8/2010 | Clevenger ............ A01N 25/08 514/1.1 |
| 2010/0249425 A1 | 9/2010 | Mutin et al. |
| 2011/0208232 A1 | 8/2011 | Lorenz |
| 2014/0328891 A1 | 11/2014 | Hunter et al. |
| 2016/0066579 A1 | 3/2016 | Porosa et al. |
| 2016/0115268 A1 | 4/2016 | Clevenger et al. |

FOREIGN PATENT DOCUMENTS

| | | |
|---|---|---|
| WO | 200100034 | 1/2001 |
| WO | 2009052352 | 4/2009 |

OTHER PUBLICATIONS

Park et al., "Antibacterial Activities of Polystyrene-Block-Poly (4-Vinyl Pyridine) and Poly (Styrene-Random-4-Vinyl Pyridine)" European Polymer Journal 40 (2004) 2318-2822, 5 pages.
Dennes et al., A Nanoscale Adhesion Layer to Promote Cell Attachment on PEEK, Feb. 18, 2009, J. Am. Chem. Soc., vol. 131, pp.
Shard et al., "Surface Oxidation of Polyethylene, Polysthylene, Polystyrene, and PEEK: The Synthon Approach", 1992, Macrmolecules, vol. 25, pp. 2053-2054.
Notification of Transmittal of the International Search Report and the Written Opinion of the International Searching Authority, or the Declaration for PCT/US17/056889 dated Jan. 5, 2018, 10 pages.

\* cited by examiner

*Primary Examiner* — Robert T Butcher

(74) *Attorney, Agent, or Firm* — Venable LLP

(57) ABSTRACT

Articles having metal, metalloid or non-metal surfaces containing an antimicrobial layer comprising antimicrobial oligomers or polymers are suitable for use in medical devices, sanitary surfaces and other applications. Antimicrobial layers contain an organophosphorus layer deposited on an article surface and antimicrobial oligomers or polymers bonded to the organophosphorus layer.

19 Claims, No Drawings

SURFACES WITH OLIGOMERIC OR POLYMERIC ANTIMICROBIALS

The invention relates to articles having antimicrobial surfaces and methods of preparing the surfaces.

BACKGROUND

The need for control of infection is a vital concern for many, from public health officials, hospital and school administrators and the like, to private citizens. Typically, control of infection can be achieved by the topical application of disinfectants, antiseptics, antibacterials and the like to surfaces likely to be contacted by infectious agents. Common disinfectants only have a short-term effect and need to be reapplied constantly.

Antibiotics can be administered to stop infection in individuals. However, such administration is not always effective. Numerous medical applications, including orthopaedic, trauma, spine and general surgery applications, where the potential for infection is a serious concern, are not amenable to simple application of antiseptic or treatment with antibiotics. For example, infection can be a devastating complication of a total joint arthroplasty (TJA). While some infections may be treated by antibiotic suppression alone, more aggressive therapies, such as two-stage re-implantation, are often required. TJA infections occur when bacteria colonize the surface of the implant. These species then form a resistant biofilm on the implant surface, which nullifies the body's normal antibody response.

External fixation devices provide temporary and necessary rigid constraints to facilitate bone healing. However, patients risk pin-tract infection at the site extending from the skin-pin interface to within the bone tissue. Such complications can result in sepsis and osteomyelitis, which could require sequestrectomy for correction. Even the most stringent pin-handling and post-procedure protocols have only a limited effect. Studies have shown that such protocols do not reduce the chance of infection.

In minimally-invasive spine fusions, pedicle screws are first implanted in the bone of the vertebrae, and then rods are fixed into the heads of the screws to immobilize and stabilize the affected segments. Screws and rods pass through the patient's skin into the spine space via a cannulated channel. As in external fixation, screws and rods are also prone to pin-tract infections; due to the implants' pathway through the skin, the chance of contacting and/or passing harmful bacteria is greatly increased.

Catheters and shunts are placed in any number of body cavities and vessels to facilitate the injection, drainage or exchange of fluids. Infections are common in catheter placements and are largely dependent on how long the patient is catheterized.

There is a need for anti-infective surfaces that may be employed in locations particularly susceptible to hosting infectious agents, such as public places, common areas of buildings, fixtures and the like. Moreover, there is a need for articles and materials with anti-infective surfaces, such as medical devices including implants, screws, rods, pins, catheters, stents, surgical tools and the like which could prevent infections by proactively killing bacteria that attempt to colonize the device surface both pre- and post-operatively.

SUMMARY

Disclosed in certain embodiments is an article having an antimicrobial surface, the article (e.g. a medical device) comprising a surface having an antimicrobial layer disposed thereon, the antimicrobial layer comprising an organophosphorus layer and antimicrobial oligomers or polymers bonded to the organophosphorus layer.

Also disclosed is in certain embodiments is a process for preparing an article having an antimicrobial surface, the process comprising depositing organophosphorus unsaturated monomers on a surface of an article (e.g. a medical device) to form an unsaturated organophosphorus layer and reacting one or more antimicrobial unsaturated monomers with the unsaturated organophosphorus layer.

Also disclosed in certain embodiments is a process for preparing an article comprising an antimicrobial surface, the process comprising depositing reactive organophosphorus compounds on a surface of the article to form a reactive organophosphorus layer, reacting the reactive organophosphorus layer with an ATRP initiator to form an initiator organophosphorus layer and reacting one or more antimicrobial unsaturated monomers with the initiator organophosphorus layer.

Other embodiments of the disclosure include methods of treating patients using the medical devices disclosed herein.

DETAILED DISCLOSURE

The antimicrobial layer comprises an organophosphorus layer attached to an article surface and antimicrobial oligomers or polymers attached to the organophosphorus layer. For instance, the antimicrobial layer comprises an oxide layer, an organophosphorus layer attached to the oxide layer through phosphinate, phosphonate or phosphate moieties and antimicrobial oligomers or polymers covalently bonded to the organophosphorus layer through the organo groups.

The oligomers or polymers are prepared for instance via free-radical polymerization techniques, discussed further below.

The oxide layer may comprise a native (natural) oxide layer or a synthetic oxide layer. Synthetic oxide surfaces include oxide, alkoxide and mixed oxide/alkoxide layers.

The term "attached" means for example covalently bonded. The organophosphorus layer may advantageously be covalently bonded to the article surface via an oxide layer.

The term "unsaturated" means ethylenically or propargylly unsaturated.

In some embodiments, the organo group may be a $C_2$-$C_{40}$ hydrocarbyl group, a $C_2$-$C_{24}$ hydrocarbyl group, or a $C_2$-$C_5$ hydrocarbyl group. Hydrocarbyl is any hydrocarbon containing group, for example straight or branched chain alkyl or alkenyl which may be interrupted by or substituted by one or more heteroatom-containing groups or aryl groups, for instance interrupted by one or more —O—, —NH— or —C(O)O— groups and/or substituted by one or more hydroxyl, carboxylic, amino, thiol, phosphonate or aryl groups. Aryl includes phenyl.

In some embodiments, the organo group may be a $C_2$, $C_3$, $C_4$, $C_5$, $C_6$, $C_7$, $C_8$, $C_9$, $C_{10}$, $C_{11}$ or $C_{12}$ hydrocarbyl group.

In some embodiments, the present articles comprise metal, metalloid or non-metal surfaces. In certain embodiments, present articles comprise ceramic, silicon, glass or fabric surfaces.

Non-metal articles/surfaces include, but are not limited to thermoplastic and thermoset polymers, thus non-metal surfaces include polymeric surfaces. Suitable polymers include, but are not limited to polyamides, polyurethanes, polyureas, polyesters, polyketones, polyimides, polysulfides, polysulfoxides, polysulfones, polythiophenes, polypyridines, polypyrroles, polyethers, silicones, polysiloxanes, polysaccharides, fluoropolymers, polyimides, polypeptides, polyethylene, polystyrene, polypropylene, glass reinforced epoxies, liquid crystal polymers, bismaleimide-triazine (BT) resins, benzocyclobutene polymers, Ajinomoto Buildup Films (ABF) and low coefficient of thermal expansion (CTE) films of glass and epoxy. In certain embodiments, suitable polymers include polyamides, polyurethanes, polyesters, polyketones, polyethers, polyimides, aramides, polyfluoroolefins, polyetheretherketones, polyetherketoneketones, epoxies, silicones and composites containing these polymers; for example polyethylene terephthalate (PET), polyamide (nylon), polyetheretherketone (PEEK) and polyetherketoneketone (PEKK).

Antimicrobial oligomers and polymers contain antimicrobial monomer units. Monomer units are reacted or "polymerized" monomers. Antimicrobial monomers are taught for instance in U.S. Pat. No. 6,355,704. Antimicrobial oligomers, polymers, monomers and monomer units contain antimicrobial moieties. Antimicrobial moieties include but are not limited to ammonium salts, pyridinium salts and phosphonium salts. Antimicrobial functional groups are also taught for instance in U.S. Pub. No. 2006/0194008.

Ammonium salts include quaternary ammonium compounds where the alkyl groups are the same or different and are for example methyl, ethyl, propyl, butyl, hexyl, heptyl or octyl.

In certain embodiments, present antimicrobial monomers contain ethylenic unsaturation. For instance, suitable antimicrobial monomers include but are not limited to (meth)acryloyloxydodecylpyridinium salts, (meth)acryloyloxyhexadecylpyridinium salts, (meth)acryloyloxydecyltriethylammonium salts, 4-hexadecyl (meth)acryloyloxyethylpyridinium salts, (meth)acryloyloxyethyl-hexadecylbipyridinium salts, (meth)acryloyloxydodecyltrimethylphosphonium salts, (meth)acryloyloxyoctadecyltriethylphosphonium salts, 4-(meth)acryloyloxy-ethyldodecylpyridinium salts, di(4-vinylbenzyl)hexadecylmethylammonium salts, di((meth)acryloyloxyethyl)dodecylmethylammonium salts and (meth)acryloyloxyethyl(4-N-hexadecylpyridinylmethyl) succinate halides. The term "(meth)acryl" means acryl or methacryl.

Anions paired with the ammonium, pyridinium and phosphonium cations include, but are not limited to halides, $F^-$, $Cl^-$, $Br^-$ or $I^-$; anions of inorganic acids such as $PO_4^{3-}$, $HPO_3^{2-}$, $H_2PO_4^-$, $Na_2PO_4^-$, $HSO_4^-$, $KSO_4^-$, $NO_3^-$, etc.; anions of organic acids such as methanesulfonic acid, acetic acid, propionic acid, benzoic acid, phenol, p-toluenesulfonic acid, maleic acid, oxalic acid, citric acid, etc. In some embodiments, anions include $AlF_6^{3-}$, $AsFe^-$, $BF_4^-$, $BiCl_4^{2-}$, $BiCl_3^{2-}$, $SbCl_6^-$, $SbF_6^-$, $PF_6^-$, $GaCl_4^-$, $InF_4^-$, $TiF_6^{2-}$, $ZrF_6^-$, $FeI_4^-$, $SnCl_6^-$, etc.

For example, suitable antimicrobial monomers include, but are not limited to methacryloyloxydodecylpyridinium bromide (MDPB), methacryloyloxyhexedecylpyridinium chloride (MHPC), 4-hexadecyhnethacryloyloxyethylpyridinium chloride (HMPC), methacryloyloxyethylhexadecylbipyridinium dichloride (MHBP), methacryloyloxyoctadecyltrimethylphosphonium chloride (DMPC), methacryloyloxyoctadecyltriethylphosphonium acetate (OEPA), 4-methacryloyloxyethyldodecylpyridinium chloride (MEDP), di(4-vinylbenzyl)hexadecylmethylammonium methylsulfate (VHMS), di(methacryloyloxyethyl)dodecylmethylammonium chloride (DDMC) and methacryloyloxyethyl(4-N-hexadecylpyridinylmethyl) succinate bromide (BMPS).

The present antimicrobial layers may be prepared via a process comprising heating an organophosphinic, organophosphonic or organophosphoric acid with an article having a native oxide or a synthetic oxide surface. This results in the formation of an organophosphorus layer where the phosphinic, phosphonic or phosphoric acid moieties are attached to the oxide surface (via phosphinate, phosphonate or phosphate groups). In some embodiments, the process includes those described in U.S. Pub. Nos. 2004/0023048 and 2010/0215643. Alternatively, present organophosphinic, organophosphonic or organophosphoric acids may be bonded with a surface via a process comprising electrochemical deposition (anodization).

In some embodiments, suitable organophosphinic, organophosphonic and organophosphoric acids contain organo groups having ethylenic or propargic unsaturation and may be referred to as organophosphorus unsaturated monomers. Monomers having ethylenic unsaturation contain for example a vinyl group, allyl group, acrylic group or methacrylic group.

Suitable organophosphinic, organophosphonic and organophosphoric acids include, but are not limited to vinyl phosphonic acid, allyl phosphonic acid, 2-methyl allylphosphonic acid, 2-butenyl phosphonic acid, allyl phosphate, ethyleneglycol methacrylatephosphate, dimethyl vinylphosphonate, diethyl allylphosphonate, bis(2-chloroethyl) vinylphosphonate, diethyl 3-butenylphosphonate, allyl phosphonic dichloride and allylphosphinic acid.

In certain embodiments, attachment of organophosphinic, organophosphonic or organophosphoric acid monomers to the article surface provides an organophosphorus layer having ethylenic or propargic unsaturation (an unsaturated organophosphorus layer).

Native oxide surfaces are found on metals including titanium, titanium alloys, stainless steel, cobalt chrome alloys, nickel, molybdenum, tantalum, zirconium, magnesium and alloys containing nickel, molybdenum, tantalum, zirconium or magnesium. Native oxide surfaces are also found on silicon surfaces.

Synthetic oxide surfaces may be imparted on metal, metalloid or non-metal surfaces. Synthetic oxide surfaces are for instance prepared by reacting a surface with a metal alkoxide as taught in U.S. Pat. No. 6,645,644 and U.S. Pub. No. 2010/0215643, optionally followed by full or partial hydrolysis. Suitable metal oxides include, but are not limited to tantalum pentethoxide, titanium tetra-t-butoxide and zirconium tetra-t-butoxide. Present synthetic oxide surfaces include metal oxides and/or metal alkoxides and/or mixed metal oxide/alkoxides.

Metals and silicon have native oxide surfaces or may be imparted with a synthetic oxide surface. For example, a titanium surface may be imparted with a zirconium oxide surface layer. In this instance, an antimicrobial layer may be attached to a titanium surface via a zirconium oxide layer.

Depositing organophosphorus unsaturated monomers on a surface may comprise reacting phosphinic acid, phosphonic acid or phosphoric acid groups with an oxide layer on the surface. Such reaction results in the attachment (e.g. by covalent bonding) of phosphinate, phosphonate or phosphate moieties to the surface.

An article surface may be coated with a continuous oxide layer, i.e., a layer that is formed by a matrix of individual molecules that are chemically bonded and linked to each other, as opposed to individual molecules covering the surface. For example, metal alkoxide molecules may be bonded together on at least a portion of a polymer surface to form a continuous layer.

An article surface may be coated with an oxide layer in a pattern or micropattern, for example via employing photoresist techniques. Thus, the antimicrobial layer may be applied in a pattern or micropattern.

The surface containing the unsaturated organophosphorus layer, where the organo group contains ethylenic unsaturation, is then reacted with ethylenicaly unsaturated antimicrobial monomers for instance via a process comprising free-radical polymerization. Conditions and reagent levels are chosen to provide a desired level of oligomerization or polymerization.

Anodization techniques that can be modified in view of the present disclosure are described for example in U.S. Pat. No. 5,126,210. For example, a metal article or metal surfaced article may optionally be cleaned with for example a mineral acid or a base to remove any surface oxides. The cleaned article may be placed in an aqueous solution or partially aqueous solution containing a suitable organophosphinic, organophosphonic or organophosphoric acid at a temperature e.g., of from about 5° C. to about 60° C. The metal surface is connected to the positive terminal of an electric power supply. A counter electrode is connected to the negative electrode of the power supply. The metal surface is then anodized at a voltage, e.g., of from about 1 to about 400 volts or more, for instance from about 30 to about 90 volts or more, depending on the desired thickness of the formed organophosphorus layer. Time periods may vary for example from about 1 second to about 60 seconds or more or from about 1 second to about 30 seconds or more.

Free-radical polymerization includes thermal techniques with the use of a free-radical initiator. Present polymerization methods also include photopolymerization. In certain embodiments, present methods comprise exposing a surface containing the unsaturated organophosphorus layer to a polymerizable antimicrobial monomer and UV light. An article surface containing an unsaturated organophosphorus layer may be coated with a suitable polymerizable antimicrobial monomer followed by exposure to UV light. A photoinitiator may be employed. Photoinitiators include, but are not limited to acylphosphine oxides and alpha-hydroxyketones as described for instance in U.S. Pat. No. 6,284,813.

Alternatively, present antimicrobial surfaces are prepared via a process comprising atom transfer radical polymerization (ATRP). In this case, an organophosphinic, organophosphonic or organophosphoric acid where the organo group contains a substituent suitable for reacting with an ATRP initiator is attached to an article surface. Suitable substituents of the organo group of organophosphorus compounds are in particular nucleophilic substituents.

Suitable organophosphinic, organophosphonic or organophosphoric acids contain as an organo group a $C_2$-$C_{40}$, a $C_2$-$C_{24}$, for example a $C_2$-$C_5$ hydrocarbyl group. The hydrocarbyl group contains one or more, for instance 1 to 3 nucleophilic substituents suitable for reacting with an ATRP initiator, for example substituents selected from hydroxyl, amino and thiol. In certain embodiments, suitable organophosphonic acids (suitable reactive organophoshorous compounds) include 11-hydroxyundecylphosphonic acid, 11-mercaptoundecylphosphonic acid and 12-mercaptododecylphosphonic acid.

In present ATRP processes, the organophosphinic, organophosphonic or organophosphoric acid compounds (reactive organophosphorus compounds) are attached to a surface as described above. The deposited layer of organophosphorus compounds containing a nucleophilic substituent is a reactive organophosphorus layer. The reactive layer is then reacted with an ATRP initiator such as alpha-bromoisobutyryl bromide. This provides an initiator organophosphorus layer. In the case of a hydroxyl substituent, this results in formation of a —$O(CO)C(CH_3)_2Br$ substituent on the organo group. Following this, ATRP is performed with unsaturated antimicrobial monomers as described above in the presence of an ATRP catalyst.

In certain embodiments, the initiator layer will contain —$(CO)C(CH_3)_2Br$ initiator substituents on a plurality of the organo groups, that is, on at least some of the organo groups. Examples of initiator substituents in the initiator layer include —$O(CO)C(CH_3)_2Br$, —$NH(CO)C(CH_3)_2Br$ and —$S(CO)C(CH_3)_2Br$.

ATRP catalysts include for example CuBr and a polyamine, such as pentamethyldiethylenetriamine.

Present antimicrobial layers prepared via ATRP may be characterized as containing antimicrobial oligomers or polymers containing a residual ATRP initiator moiety such as —$O(CO)C(CH_3)_2$—, —$NH(CO)C(CH_3)_2$— or —$S(CO)C(CH_3)_2$—.

Advantageously, reactive organophosphorus compounds may be deposited by a process comprising anodization followed by a process comprising ATRP to form an antimicrobial layer containing antimicrobial oligomers or polymers.

An article surface may advantageously be treated with oxygen plasma prior to deposition of organophosphorus unsaturated monomers or reactive organophosphorus compounds and/or prior to preparation of a synthetic oxide layer. The term "oxygen plasma" means an oxygen source having a portion of the molecules ionized. In certain embodiments, the source of the oxygen plasma can be $O_2$, air or a combination thereof. In other embodiments, the source of oxygen plasma is any gaseous mixture that has any amount of oxygen.

Non-antimicrobial monomers may also be employed, resulting in oligomers/polymers containing antimicrobial and non-antimicrobial monomers. Non-antimicrobial monomers include, but are not limited to hydroxyalkyl acrylates or methacrylates, for example, methyl, ethyl, butyl, 2-ethylhexyl- or 2-hydroxyethyl acrylate, isobornyl acrylate or methyl or ethyl methacrylate. Silicone acrylates may also be included. Further examples include acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride and vinylidene chloride. Also optionally included are monomers containing two or more double bonds such as diacrylates of ethylene glycol, propylene glycol, neopentyl glycol, hexamethylene glycol and of bisphenol-A, such as 4,4'-bis(2-acryloyloxyethoxy)diphenylpropane, trimethylolpropane triacrylate, pentaerythritol triacrylate or tetraacrylate, vinyl acrylate, divinyl benzene, divinyl succinate, diallyl phthalate, triallyl phosphate, triallyl isocyanurate and tris(2-acryloylethyl) isocyanurate.

In certain embodiments, the antimicrobial oligomers or polymers of the invention contain for example from 2 to about 50,000 or more antimicrobial monomer units, for instance from about 3, about 4, about 5, about 7, about 10, about 20, about 30, about 40, about 50 or about 60 to about 70, about 80, about 90, about 100, about 125, about 150, about 175, about 200, about 300, about 400, about 500, about 600, about 700, about 800, about 900, about 1000, about 2000, about 3000, about 5000 or about 10000 antimicrobial monomer units.

In other embodiments, the antimicrobial oligomers or polymers of the invention contain for example from any one of about 2, about 3, about 4, about 5, about 7, about 10, about 20, about 30, about 40, about 50 or about 60 to about 70, about 80, about 90, about 100, about 125, about 150, about 175, about 200, about 300, about 400, about 500, about 600, about 700, about 800, about 900, about 1,000 monomer units to any one of about 1,500, about 2,000, about 3,000, about 5,000, bout 10,000, about 25,000, about 40,000 or about 50,000 antimicrobial monomer units.

Organophosphorus layers of the invention may comprise a complete or partial mono-layer of organophosphorus monomers or compounds. Alternatively, they may comprise complete or partial multi-layers of the organophosphorus monomers or compounds, for instance from 1 to about 2, about 3, about 4, about 5, about 6, about 7, about 8, about 9 or about 10 complete or partial layers.

Present articles are for instance medical devices such as implantable or percutaneous medical devices. Medical devices include endoscopic, arthroscopic, laproscopic, cardiac, cardiovascular, vascular, non-woven mesh, woven mesh, foam, cloth, fabric, orthopedic, orthopedic trauma, spine, surgical, drainage catheter, shunt, tape, meshes, rope, cable, wire, suture, skin and tissue staple, burn sheet, external fixation and temporary/non-permanent implant devices.

In certain embodiments the article is a medical implant device or component thereof. Suitable medical implant devices and components thereof include, but not limited to, orthopedic prostheses for the hip, knee, ankle, shoulder, elbow, and spine. Exemplary medical implant devices include a full or partial knee arthroplasty prosthesis, full or partial hip arthroplasty prosthesis, full or partial elbow arthroplasty prosthesis, full or partial wrist arthroplasty prosthesis, full or partial shoulder arthroplasty prosthesis, full or partial ankle arthroplasty prosthesis, and full or partial articulating spinal segment arthroplasty prosthesis. Exemplary components of medical implant devices include a femoral component (e.g., for replacing one or more femoral condyles) or a tibial component (e.g., for replacing at least a portion of a proximal tibial plateau) of a knee prosthesis (e.g., a uni-compartmental or total knee arthroplasty prosthesis), a femoral component (e.g., for replacing at least the proximal portion or head of the femur) or an acetabular cup (e.g., for replacing the hip bone's femoral socket) of a hip prosthesis, a humeral component (e.g., for replacing the distal portion of the humerus) or an ulnar component (e.g., for replacing the proximal portion of the ulna) of an elbow prosthesis, a metacarpal component (for replacing at least a portion of one or more metacarpal bones) or radial component (for replacing the distal portion of the radius) of a wrist prosthesis, a humeral component (e.g., for replacing the proximal portion or head of the humerus) or glenoid component (e.g., for replacing the glenoid or socket portion of the scapula) of a shoulder prosthesis, a tibial component (e.g., for replacing the distal portion of the tibia) or talar component (e.g., for replacing the proximal portion of the talus) of an ankle prosthesis, and an endplate component (e.g., for contacting the superior or inferior portion of a cervical, lumbar or thoracic vertebra) or spacer component (e.g. for insertion between endplate components) of a vertebral disc prosthesis.

Present articles also include for example household articles such as cutting boards, sinks, utensils, counter tops, packaging, food storage containers, refrigerator parts, coolers and the like.

Present articles also include for example articles employed in hospital and/or nursing home environments such as walls, floors, bed-pans and woven or non-woven surfaces such as surgical garments, draperies, linens, bandages, wound dressings and the like.

Following are some embodiments of the invention.

In a first embodiment, an article comprising a surface having an antimicrobial layer disposed thereon, the antimicrobial layer comprising an organophosphorus layer and antimicrobial oligomers or polymers bonded to the organophosphorus layer.

In a second embodiment, an article according to the first embodiment wherein the organophosphorus layer comprises organophosphonate moieties. In a third embodiment, an article according to the first or second embodiment, wherein the organophosphorus layer comprises organophosphinate moieties. In a fourth embodiment, an article according to any of the preceding embodiments, wherein the organophosphorus layer comprises organophosphate moieties.

In a fifth embodiment, an article according to any of the preceding embodiments comprising a metal surface. In a sixth embodiment, an article according to any of the preceding embodiments, wherein the surface comprises titanium, a titanium alloy, stainless steel, a cobalt chrome alloy, nickel, molybdenum, tantalum, zirconium, magnesium or an alloy containing one or more of nickel, molybdenum, tantalum, zirconium and magnesium. In a seventh embodiment, an article according to any of the preceding embodiments, wherein the surface comprises titanium.

In an eighth embodiment, an article according to any of embodiments 1-4, comprising a polymeric surface. In a ninth embodiment, an article according to any of the first through fourth embodiments, wherein the surface comprises a polyamide, a polyurethane, a polyurea, a polyester, a polyketone, a polyimide, a polysulfide, a polysulfoxide, a polysulfone, a polythiophene, a polypyridine, a polypyrrole, a polyether, a silicone, a polysiloxane, a polysaccharide, a fluoropolymer, a polyimide, a polypeptide, polyethylene, polystyrene, polypropylene, a glass reinforced epoxy, a liquid crystal polymer, a bismaleimide-triazine (BT) resin, a benzocyclobutene polymer, an Ajinomoto Buildup Film (ABF) or a low coefficient of thermal expansion (CTE) film of glass and epoxy. In a tenth embodiment, an article according to any of embodiments 1-4, wherein the surface comprises polyethylene terephthalate (PET), a polyamide, a polyetheretherketone (PEEK) or a polyetherketoneketone (PEKK).

In an eleventh embodiment, an article according to any of the preceding embodiments, wherein the organo group comprises a $C_2$-$C_{40}$ or a $C_2$-$C_{24}$ hydrocarbyl group. In a twelfth embodiment, an article according to any of the preceding embodiments, wherein the organo group comprises a $C_2$-$C_5$ hydrocarbyl group.

In a thirteenth embodiment, an article according to any of the preceding embodiments, wherein the antimicrobial oligomers or polymers comprise ammonium salts, pyridinium salts or phosphonium salts. In a fourteenth embodiment, an article according to any of the preceding embodiments, wherein the antimicrobial oligomers or polymers comprise one or more antimicrobial monomer units of monomers selected from the group consisting of methacryloyloxydodecylpyridinium salts, methacryloyloxyhexadecylpyridinium salts, methacryloyloxydecyltriethylammonium salts, 4-hexadecylmethacryloyloxyethylpyridinium salts, methacryloyloxyethylhexadecylbipyridinium salts, methacryloyloxydodecyltrimethylphosphonium salts, methacryloyloxyoctadecyltriethylphosphonium salts, 4-methacryloyloxyethyldodecylpyridinium salts, di(4-vinylbenzyl)hexadecylmethylammonium salts, di(methacryloyloxyethyl)dodecylmethylammonium salts and methacryloyloxyethyl(4-N-hexadecylpyridinylmethyl) succinate halides.

In a fifteenth embodiment, an article according to any of the preceding embodiments, wherein the antimicrobial oligomers or polymers contain pyridinium salts.

In a sixteenth embodiment, an article according to any of the preceding embodiments, wherein the antimicrobial layer further comprises a native oxide layer. In a seventeenth embodiment, an article according to any of the preceding embodiments, wherein the antimicrobial layer further comprises a synthetic oxide layer.

In an eighteenth embodiment, an article according to any of the preceding embodiments, wherein the antimicrobial layer further comprises an oxide layer and where the organophosphorus layer is covalently bonded to the oxide layer through phosphinate, phosphonate or phosphate moieties.

In a nineteenth embodiment, an article according to any of the preceding embodiments, wherein the antimicrobial layer is continuous.

In a twentieth embodiment, an article according to any of embodiments 1-19 selected from the group consisting of endoscopic, arthroscopic and laproscopic medical devices. In a twenty first embodiment, an article according to any of embodiments 1-19 selected from the group consisting of cardiac, cardiovascular, vascular, orthopedic, orthopedic trauma and spine medical devices. In a twenty second embodiment, an article according to any of embodiments 1-19 selected from the group consisting of catheters, shunts, tapes, meshes, ropes, cables, wires, sutures, skin or tissue staples, burn sheets, external fixation devices and temporary implants.

In a twenty third embodiment, an article according to any of the preceding embodiments, wherein the antimicrobial layer is disposed on the surface in a pattern or micropattern.

In a twenty fourth embodiment, an article according to any of the preceding embodiments, wherein the antimicrobial oligomers or polymers comprise identical antimicrobial monomer units. In a twenty fifth embodiment, an article according to any of embodiments 1-23, wherein the antimicrobial oligomers or polymers comprise two or more different antimicrobial monomer units.

In a twenty sixth embodiment, an article according to any of the preceding embodiments, wherein the antimicrobial oligomers or polymers further contain non-antimicrobial monomer units.

In a twenty seventh embodiment, an article according to any of the preceding embodiments, wherein the antimicrobial oligomers or polymers contain a —O(CO)C(CH$_3$)$_2$—, —NH(CO)C(CH$_3$)$_2$— or a —S(CO)C(CH$_3$)$_2$— moiety.

In a twenty eighth embodiment, a process for preparing an article comprising an antimicrobial surface, the process comprising depositing organophosphorus unsaturated monomers on a surface of the article to form an unsaturated organophosphorus layer and reacting one or more antimicrobial unsaturated monomers with the unsaturated organophosphorus layer.

In a twenty ninth embodiment, a process according to the twenty eighth embodiment, wherein the organophosphorus monomers comprise organophosphonic acids. In a thirtieth embodiment, a process according to embodiments 28 or 29 where the organophosphorus monomers comprise organophosphinic acids. In a thirty first embodiment, a process according to any of embodiments 28-30, wherein the organophosphorus monomers comprise organophosphoric acids.

In a thirty second embodiment, a process according to any of embodiments 28-31, wherein the article comprises a metal surface. In a thirty third embodiment, a process according to any of embodiments 28-32, wherein the article comprises a surface comprising titanium, a titanium alloy, stainless steel, a cobalt chrome alloy, nickel, molybdenum, tantalum, zirconium, magnesium or an alloy containing one or more of nickel, molybdenum, tantalum, zirconium and magnesium. In a thirty fourth embodiment, a process according to any of embodiments 28-33, wherein the article surface comprises titanium.

In a thirty fifth embodiment, a process according to any of embodiments 28-31, wherein the article comprises a polymeric surface. In a thirty sixth embodiment, a process according to any of embodiments 28-31, wherein the article comprises a surface comprising a polyamide, a polyurethane, a polyurea, a polyester, a polyketone, a polyimide, a polysulfide, a polysulfoxide, a polysulfone, a polythiophene, a polypyridine, a polypyrrole, a polyether, a silicone, a polysiloxane, a polysaccharide, a fluoropolymer, a polyimide, a polypeptide, polyethylene, polystyrene, polypropylene, a glass reinforced epoxy, a liquid crystal polymer, a bismaleimide-triazine (BT) resin, a benzocyclobutene polymer, an Ajinomoto Buildup Film (ABF) or a low coefficient of thermal expansion (CTE) film of glass and epoxy. In a thirty seventh embodiment, a process according to any of embodiments 28-31, wherein the article surface comprises polyethylene terephthalate (PET), a polyamide, a polyetheretherketone (PEEK) or a polyetherketoneketone (PEKK).

In a thirty eighth embodiment, a process according to any of embodiments 28-37, wherein the organo group comprises a $C_2$-$C_{40}$ or $C_2$-$C_{24}$ hydrocarbyl group. In a thirty ninth embodiment, a process according to any of embodiments 28-38, wherein the organo group comprises a $C_2$-$C_5$ hydrocarbyl group.

In a fortieth embodiment, a process according to any of embodiments 28-39, wherein the antimicrobial monomers comprise ammonium salts, pyridinium salts or phosphonium salts. In a forty first embodiment, a process according to any of embodiments 28-40, wherein the antimicrobial monomers are selected from the group consisting of methacryloyloxydodecylpyridinium salts, methacryloyloxyhexadecylpyridinium salts, methacryloyloxydecyltriethylammonium salts, 4-hexadecylmethacryloyloxyethylpyridinium salts, methacryloyloxyethylhexadecylbipyridinium salts, methacryloyloxydodecyltrimethylphosphonium salts, methacryloyloxyoctadecyltriethylphosphonium salts, 4-methacryloyloxyethyldodecylpyridinium salts, di(4-vinylbenzyl)hexadecylmethylammonium salts, di(methacryloyloxyethyl)dodecylmethylammonium salts and methacryloyloxyethyl(4-N-hexadecylpyridinylmethyl) succinate halides. In a forty second embodiment, a process according to any of embodiments 28-41, wherein the antimicrobial monomers contain pyridinium salts.

In a forty third embodiment, a process according to any of embodiments 28-42, wherein the organophosphorus unsaturated monomers are selected from the group consisting of vinyl phosphonic acid, allyl phosphonic acid, 2-methyl allylphosphonic acid, 2-butenyl phosphonic acid, allyl phosphate and ethyleneglycol methacrylatephosphate.

In a forty fourth embodiment, a process according to any of embodiments 28-43, wherein the antimicrobial surface comprises a continuous antimicrobial layer.

In a forty fifth embodiment, a process according to any of embodiments 28-44, wherein the article is selected from the group consisting of endoscopic, arthroscopic and laproscopic medical devices. In a forty sixth embodiment, a process according to any of embodiments 28-44, wherein the article is selected from the group consisting of cardiac, cardiovascular, vascular, orthopedic, orthopedic trauma and spine medical devices. In a forty seventh embodiment, a process according to any of embodiments 28-44, wherein the article is selected from the group consisting of catheters, shunts, tapes, meshes, ropes, cables, wires, sutures, skin or tissue staples, burn sheets, external fixation devices and temporary implants.

In a forty eighth embodiment, a process according to any of embodiments 28-47, wherein the antimicrobial surface comprises an antimicrobial layer disposed on the surface in a pattern or micropattern.

In a forty ninth embodiment, a process according to any of embodiments 28-48, wherein the antimicrobial monomers are identical. In a fiftieth embodiment, a process according to any of embodiments 28-48, wherein the antimicrobial monomers comprise two or more different monomers.

In a fifty first embodiment, a process according to any of embodiments 28-50, comprising also reacting the unsaturated organophosphorus layer with non-antimicrobial monomers.

In a fifty second embodiment, a process according to any of embodiments 28-51, comprising thermal treatment to form the unsaturated organophosphorus layer.

In a fifty third embodiment, a process according to any of embodiments 28-52, wherein the article surface comprises a native oxide layer. In a fifty fourth embodiment, a process according to any of embodiments 28-53, wherein the article surface comprises a synthetic oxide layer.

In a fifty fifth embodiment, a process according to the fifty second embodiment, wherein the thermal treatment forms the unsaturated organophosphorus layer covalently bonded to an oxide layer through phosphinate, phosphonate or phosphate moieties.

In a fifty sixth embodiment, a process according to any of embodiments 28-34 and 38-51, wherein depositing the organophosphorus monomers on the article surface comprises anodization. In a fifty seventh embodiment, a process according to the fifty sixth embodiment, comprising preparing an aqueous solution containing organophosphorus unsaturated monomers, placing an article having a metal surface in the aqueous solution, connecting the metal surface to a positive terminal of an electric power supply and connecting a counter electrode to a negative electrode of the power supply. In a fifty eighty embodiment, a process according to the fifty seventh embodiment, comprising applying a voltage of from about 1 to about 400 volts or more or from about 30 to about 90 volts or more for a time period of from about 1 sec to about 60 seconds or more or from about 1 second to about 30 seconds or more.

In a fifty ninth embodiment, a process for preparing an article comprising an antimicrobial surface, the process comprising depositing reactive organophosphorus compounds on a surface of an article to form a reactive organophosphorus layer, reacting the reactive organophosphorus layer with an ATRP initiator to form an initiator organophosphorus layer and reacting one or more antimicrobial unsaturated monomers with the initiator organophosphorus layer.

In a sixtieth embodiment, a process according to the fifty ninth embodiment, wherein the organophosphorus compounds comprise organophosphonic acids. In a sixty first embodiment, a process according to the fifty ninth embodiment, wherein the organophosphorus compounds comprise organophosphinic or organophosphoric acids.

In a sixty second embodiment, a process according to any of embodiments 59-61, wherein the article comprises a metal surface. In a sixty third embodiment, a process according to any of embodiments 59-62, wherein the article comprises a surface comprising titanium, a titanium alloy, stainless steel, a cobalt chrome alloy, nickel, molybdenum, tantalum, zirconium, magnesium or an alloy containing one or more of nickel, molybdenum, tantalum, zirconium and magnesium. In a sixty fourth embodiment, a process according to any of embodiments 59-63, wherein the article surface comprises titanium.

In a sixty fifth embodiment, a process according to any of embodiments 59-61, wherein the article comprises a polymeric surface. In a sixty sixth embodiment, a process according to any of embodiments 59-61, wherein the article comprises a surface comprising a polyamide, a polyurethane, a polyurea, a polyester, a polyketone, a polyimide, a polysulfide, a polysulfoxide, a polysulfone, a polythiophene, a polypyridine, a polypyrrole, a polyether, a silicone, a polysiloxane, a polysaccharide, a fluoropolymer, a polyimide, a polypeptide, polyethylene, polystyrene, polypropylene, a glass reinforced epoxy, a liquid crystal polymer, a bismaleimide-triazine (BT) resin, a benzocyclobutene polymer, an Ajinomoto Buildup Film (ABF) or a low coefficient of thermal expansion (CTE) film of glass and epoxy. In a sixty seventh embodiment, a process according to any of embodiments 59-61, wherein the article surface comprises polyethylene terephthalate (PET), a polyamide, a polyetheretherketone (PEEK) or a polyetherketoneketone (PEKK).

In a sixty eighth embodiment, a process according to any of embodiments 59-67, wherein the organo group comprises a $C_2$-$C_{40}$ or $C_2$-$C_{24}$ hydrocarbyl group containing one or more nucleophilic substituents. In a sixty ninth embodiment, a process according to any of embodiments 59-68, wherein the organo group comprises a $C_2$-$C_{40}$ hydrocarbyl group containing a substituent selected from hydroxyl, amino and thiol.

In a seventieth embodiment, a process according to any of embodiments 59-69, wherein the antimicrobial monomers comprise ammonium salts, pyridinium salts or phosphonium salts. In a seventy first embodiment, a process according to any of embodiments 59-70, wherein the antimicrobial monomers are selected from the group consisting of methacryloyloxydodecylpyridinium salts, methacryloyloxyhexadecylpyridinium salts, methacryloyloxydecyltriethylammonium salts, 4-hexadecylmethacryloyloxyethylpyridinium salts, methacryloyloxyethylhexadecylbipyridinium salts, methacryloyloxydodecyltrimethylphosphonium salts, methacryloyloxyoctadecyltriethylphosphonium salts, 4-methacryloyloxyethyldodecylpyridinium salts, di(4-vinylbenzyl)hexadecylmethylammonium salts, di(methacryloyloxyethyl)dodecylmethylammonium salts and methacryloyloxyethyl(4-N-hexadecylpyridinylmethyl)succinate halides. In a seventy second embodiment, a process according to any of embodiments 59-71, wherein the antimicrobial monomers contain pyridinium salts.

In a seventy third embodiment, a process according to any of embodiments 59-72, wherein the initiator organophosphorus layer contains an initiator moiety selected from —O(CO)C(CH$_3$)$_2$Br, —NH(CO)C(CH$_3$)$_2$Br and —S(CO)C(CH$_3$)$_2$Br.

In a seventy fourth embodiment, a process according to any of embodiments 59-73, wherein the antimicrobial surface comprises a continuous antimicrobial layer.

In a seventy fifth embodiment, a process according to any of embodiments 59-74, wherein the article is selected from the group consisting of endoscopic, arthroscopic and laproscopic medical devices. In a seventy sixth embodiment, a process according to any of embodiments 59-77, wherein the article is selected from the group consisting of cardiac, cardiovascular, vascular, orthopedic, orthopedic trauma and spine medical devices. In a seventy seventh embodiment, a process according to any of embodiments 59-74, wherein the article is selected from the group consisting of catheters, shunts, tapes, meshes, ropes, cables, wires, sutures, skin or tissue staples, burn sheets, external fixation devices and temporary implants.

In a seventy eighth embodiment, a process according to any of embodiments 59-77, wherein the antimicrobial surface comprises an antimicrobial layer disposed on the surface in a pattern or micropattern.

In a seventy ninth embodiment, a process according to any of embodiments 59-78, wherein the antimicrobial monomers are identical. In an eightieth embodiment, a process according to any of embodiments 59-78, wherein the antimicrobial monomers comprise two or more different monomers.

In an eighty first embodiment, a process according to any of embodiments 59-80, comprising also reacting the initiator organophosphorus layer with non-antimicrobial monomers.

In an eighty second embodiment, a process according to any of embodiments 59-81, comprising thermal treatment to form the reactive organophosphorus layer.

In an eighty third embodiment, a process according to any of embodiments 59-82, wherein the article surface comprises a native oxide layer. In an eighty fourth embodiment, a process according to any of embodiments 59-83, wherein the article surface comprises a synthetic oxide layer.

In an eighty fifth embodiment, a process according to the eighty second embodiment, wherein the thermal treatment forms the reactive organophosphorus layer covalently bonded to an oxide layer through phosphinate, phosphonate or phosphate moieties.

In an eighty sixth embodiment, a process according to any of embodiments 59-64 and 68-81, wherein depositing the organophosphorus compounds on the article surface comprises anodization.

In an eighty seventh embodiment, a process according to the eighty sixth embodiment, comprising preparing an aqueous solution containing organophosphorus unsaturated monomers, placing an article having a metal surface in the aqueous solution, connecting the metal surface to a positive terminal of an electric power supply and connecting a counter electrode to a negative electrode of the power supply.

In an eighty eighth embodiment, a process according to the eighty seventh embodiment, comprising applying a voltage of from about 1 to about 400 volts or more or from about 30 to about 90 volts or more for a time period of from about 1 sec to about 60 seconds or more or from about 1 second to about 30 seconds or more.

In an eighty ninth embodiment, a process according to any of embodiments 28-88, comprising treating a surface of the article with oxygen plasma prior to depositing the organophosphorus unsaturated monomers or depositing the reactive organophosphorus compounds on the surface.

In present processes of forming an unsaturated organophosphorus layer or a reactive organophosphorus layer on a surface of an article, wherein the layer formation comprises thermal treatment, the thermal treatment may advantageously be performed under reduced pressure at elevated temperature. The process may also include a step of placing the article under an inert atmosphere prior to reduced pressure. Temperatures in some embodiments may be from any one of about 100° C., about 110° C., about 120° C., about 130° C. or about 140° C. to any one of about 150° C., about 160° C., about 170° C., about 180° C., about 190° C., about 200° C., about 210° C. or higher. Reduced pressure in some embodiments may be from any one of about 0.1 torr, about 1 torr, about 5 torr, about 10 torr, about 30 torr, about 75 torr or about 100 torr to any one of about 150 torr, about 200 torr, about 250 torr, about 300 torr, about 350 torr or about 400 torr. The thermal processes performed under reduced pressure at an elevated temperature may in some embodiments be performed for a time period from any one of about 0.5 hours, about 1 hour, 1.5 hours, about 2 hours or about 3 hours to about 4 hours, about 5 hours, about 6 hours, about 7 hours, about 8 hours, about 9 hours or about 10 hours.

The articles "a" and "an" herein refer to one or to more than one (e.g. at least one) of the grammatical object. Any ranges cited herein are inclusive. The term "about" used throughout is used to describe and account for small fluctuations. For instance, "about" may mean the numeric value may be modified by ±5%, ±4%, ±3%, ±2%, ±1%, ±0.5%, ±0.4%, ±0.3%, ±0.2%, ±0.1% or ±0.05%. All numeric values are modified by the term "about" whether or not explicitly indicated. Numeric values modified by the term "about" include the specific identified value. For example "about 5.0" includes 5.0.

Unless otherwise indicated, all parts and percentages are by weight.

All U.S. patent applications, published patent applications and patents referred to herein are hereby incorporated by reference.

Example 1

Anodization

A clean metal titanium strip is placed in a 15 weight % aqueous solution of vinyl phosphonic acid. A titanium counter electrode is attached to the negative terminal of a DC power supply. The voltage is adjusted to between 1 and 300V and a titanium rod connected to the positive terminal of the power supply is contacted with the titanium strip for a period of from 1 to 30 seconds.

Anodization occurs, resulting in formation of a titanium oxide layer and vinyl phosphonic acid bonded to the oxide layer via phosphonate moieties. Ti—O—P fragments are observed via TOF-SIMS surface analysis. The titanium surface having an attached unsaturated organophosphorus layer is represented as below.

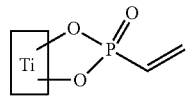

A solution of 12-methacryloyloxydodecylpyridinium bromide (MDPB) in ethanol (1 g/70 mL) is sprayed onto the titanium surface containing the vinylphosphonate layer (unsaturated organophosphorus layer). The titanium strips are placed in a nitrogen purged UV ozone cleaner chamber and exposed to UV light with a lambda max of ca. 260 nm with continuous purging for 15 minutes, resulting in polymerization of the vinyl groups with the methacrylate groups.

A titanium strip containing an antimicrobial layer is formed. The antimicrobial layer attached to a titanium surface contains an oxide layer, an organophosphorus layer and an antimicrobial polymer containing antimicrobial monomer units, as represented below, where * is a terminal end group.

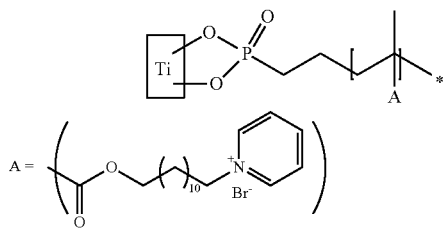

Example 2

ATRP

A clean titanium screw is placed in a 15 mM solution of 11-hydroxyundecylphosphonic acid in ethanol for 30 minutes, is removed and is air dried. The organophosphonic acid coated screw is placed in an oven set at 170° C. under reduced pressure for 4 hours. The screw is allowed to cool under vacuum. Presence of the organophosphonate on the titanium surface is confirmed by IR spectroscopy. A portion of the attached organophosphorus layer comprising an organophosphonate moiety is represented as below (a reactive organophosphorus layer).

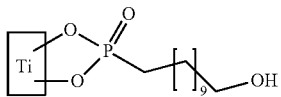

The coated screw is placed into a stirred bath of 250 mL methylene chloride. To the solvent is added dropwise 3 mL of triethylamine followed by 2 mL alpha-bromoisobutyryl bromide. The mixture is stirred for 4 hours at 25° C., the screw is removed and is dried with a stream of argon followed by vacuum to provide an organophosphorus layer containing an ATRP initiator moiety as represented below (initiator organophosphorus layer).

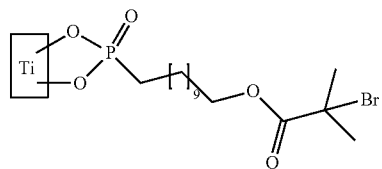

The titanium screw containing an undecylphosphonate layer now substituted at the 11-position with —O(CO)C(CH$_3$)$_2$Br is placed in an aqueous solution of 12-methacryloyloxydodecylpyridinium bromide (MDPB) (7.83 g/470 mL). The solution is purged with argon and is stirred under an argon atmosphere.

A catalyst is prepared by adding 52 mL water to a stirred flask. The system is purged with argon and placed under an argon atmosphere. To the stirred water is added 653 mg of CuBr and 1.31 mL pentamethyldiethylenetriamine. Stirring is continued for 30 minutes.

The catalyst solution is added dropwise via a syringe to the MDPB containing mixture and the mixture is stirred under argon for 4 hours. The screw is removed, is washed with alcohol and is dried with a stream of argon followed by vacuum.

A titanium article containing an antimicrobial layer attached to a surface thereof is formed. The antimicrobial layer contains an oxide layer, an organophosphorus layer and an antimicrobial polymer containing antimicrobial monomer units, as represented below. The monomer units are MDPB monomer units.

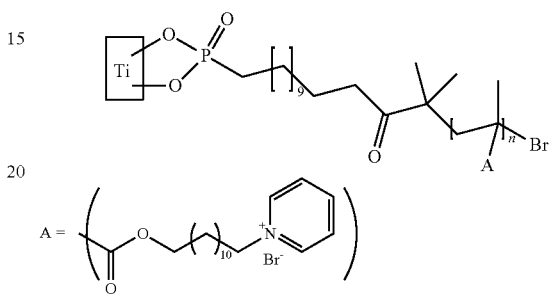

Example 3

ATRP

A titanium plate is cleaned with by placing it in a commercial detergent, followed by sonication, water rinse and drying under reduced pressure. The titanium plate is placed in a quartz chamber and treated with oxygen plasma at 25 W. An antimicrobial layer is attached to the titanium plate as in Example 2, employing 11-hydroxyundecylphosphonic acid and MDPB antimicrobial monomer.

Example 4

Antimicrobial Efficacy

Titanium strips according to Example 1 and untreated samples are cut into 1×1 cm squares, sanitized with 70% alcohol and dried with argon. The sanitized samples are aseptically transferred individually into the wells of a sterile 24-well polystyrene dish. An overnight culture of MSSA 29213 is diluted in ASTM E2149 working buffer (0.3 mM KH$_2$PO$_4$, pH 7.2) to OD$_{600}$=0.005 (~1-4E+06 CFU/mL).

A 330 mL portion of the bacterial dilution is pipetted into each of the wells to cover the samples. A sample of the bacterial dilution is also serially diluted in 1×DPBS (Dulbecco's phosphate-buffered saline) and drop plated in triplicate on a TSA plate to ensure the bacterial challenge is on target. The TSA (tryptone soya agar) plates are incubated overnight at 37° C.

The polystyrene dish is placed into the 37° C. incubator at 500 RPM on a IKA MS3 digital shaker with a microtiter plate attachment overnight (18±2 hours). After the overnight incubation, the 24-well plate containing the sample buffer is removed from the incubator and the buffer samples are pipetted into a 96-well plate and serially diluted 1:10 in 1×DPBS. Each dilution is drop plated in triplicate for each sample on TSA plates. The plates are incubated overnight at 37° C. Against MSSA 21293, treated coupons show a reduction vs. control of 99.92% this assay.

The invention claimed is:

1. An article comprising:
a surface having an antimicrobial layer disposed thereon, the antimicrobial layer comprising:
an organophosphorus layer and antimicrobial oligomers or polymers bonded to the organophosphorus layer,
wherein the surface comprises a metal selected from a group consisting of titanium, a titanium alloy, stainless steel, a cobalt chrome alloy, nickel, molybdenum, tantalum, zirconium, magnesium, and an alloy containing at least one of nickel, molybdenum, tantalum, zirconium and magnesium,
wherein the antimicrobial oligomers or polymers comprise about 3 to about 50,000 repeating antimicrobial monomer units, and
wherein the antimicrobial monomer units comprise ammonium salts or pyridinium salts.

2. An article according to claim 1, wherein the surface comprises titanium.

3. An article according to claim 1, wherein the antimicrobial oligomers or polymers comprise pyridinium salts.

4. An article according to claim 1, wherein the antimicrobial oligomers or polymers comprise ammonium salts.

5. An article according to claim 1, wherein the antimicrobial oligomers or polymers comprise one or more antimicrobial monomer units of monomers selected from the group consisting of methacryloyloxydodecylpyridinium salts, methacryloyloxyhexadecylpyridinium salts, 4-hexadecylmethacryloyloxyethylpyridinium salts, methacryloyloxyethylhexadecylbipyridinium salts, 4-methacryloyloxyethyldodecylpyridinium salts and methacryloyloxyethyl(4-N-hexadecylpyridinylmethyl) succinate halides.

6. An article according to claim 1, wherein the antimicrobial oligomers or polymers comprise one or more antimicrobial monomer units of monomers selected from the group consisting of methacryloyloxydecyltriethylammonium salts, di(4-vinylbenzyl)hexadecylmethylammonium salts and di(methacryloyloxyethyl)dodecylmethylammonium salts.

7. An article according to claim 1, wherein the antimicrobial oligomers or polymers comprise one or more antimicrobial monomer units selected from the group consisting of methacryloyloxydodecylpyridinium bromide, methacryloyloxyhexedecylpyridinium chloride, 4-hexadecyhnethacryloyloxyethylpyridinium chloride, methacryloyloxyethylhexadecylbipyridinium dichloride, 4-methacryloyloxyethyldodecylpyridinium chloride and methacryloyloxyethyl(4-N-hexadecylpyridinylmethyl) succinate bromide.

8. An article according to claim 1, wherein the organophosphorus comprises a $C_2$-$C_{24}$ hydrocarbyl group.

9. An article according to claim 1, wherein the organophosphorus comprises a $C_2$-$C_5$ hydrocarbyl group.

10. An article according to claim 1, wherein the antimicrobial oligomers or polymers contain a O(CO)C(CH$_3$)$_2$—, —NH(CO)C(CH$_3$)$_2$— or a —S(CO)C(CH$_3$)$_2$— moiety.

11. An article according to claim 1, wherein the antimicrobial layer comprises an oxide layer and wherein the organophosphorus layer is covalently bonded to the oxide layer through phosphinate, phosphonate or phosphate moieties.

12. An article according to claim 1, wherein the antimicrobial layer comprises an oxide layer and wherein the organophosphorus layer is covalently bonded to the oxide layer through phosphonate moieties.

13. An article according to claim 1, wherein the antimicrobial layer comprises a native oxide layer.

14. An article according to claim 1, wherein the antimicrobial layer is continuous.

15. An article according to claim 1, wherein the antimicrobial layer is disposed on the surface in a pattern or micropattern.

16. An article according to claim 1, selected from the group consisting of medical devices and implants.

17. An article according to claim 1, selected from the group consisting of endoscopic, arthroscopic and laparascopic medical devices.

18. An article according to claim 1, selected from the group consisting of cardiac, cardiovascular, vascular, orthopedic, orthopedic trauma and spine medical devices.

19. An article according to claim 1, selected from the group consisting of catheters, shunts, tapes, meshes, ropes, cables, wires, sutures, skin or tissue staples, burn sheets, external fixation devices and temporary implants.

* * * * *